(12) United States Patent
Yamamoto et al.

(10) Patent No.: US 6,436,255 B2
(45) Date of Patent: Aug. 20, 2002

(54) BIOSENSOR

(75) Inventors: Tomohiro Yamamoto, Hirakata; Motokazu Watanabe; Shin Ikeda, both of Katano; Shiro Nankai, Hirakata, all of (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/764,142

(22) Filed: Jan. 19, 2001

(30) Foreign Application Priority Data

Jan. 21, 2000 (JP) .......................... 2000-013025

(51) Int. Cl.[7] ............................. G01N 27/327
(52) U.S. Cl. ........................................... 204/403
(58) Field of Search ............................ 204/403

(56) References Cited

FOREIGN PATENT DOCUMENTS

| JP | 61-294351 | 12/1986 |
|---|---|---|
| JP | 2-62952 | 3/1990 |
| JP | 2000-39416 | 2/2000 |

Primary Examiner—T. Tung
Assistant Examiner—Alex Noguerola
(74) Attorney, Agent, or Firm—McDermott, Will & Emery (57) ABSTRACT

The present invention provides a biosensor which enables prompt quantification by facilitating introduction of a sample solution even when the amount of the sample solution is small and improving dissolution of reagents. The biosensor comprises an insulating base plate; an electrode system including at least a measuring electrode and a counter electrode formed on the base plate; a cover member integrated into the base plate to form a sample solution supply pathway for supplying a sample solution to the electrode system between the cover member and the base plate; a reaction reagent system including at least an electron mediator and an oxidoreductase; and a carrier supporting at least the electron mediator or the oxidoreductase of the reaction reagent system, wherein the carrier is partially or wholly disposed outside the sample solution supply pathway.

13 Claims, 5 Drawing Sheets

BIOSENSOR

BACKGROUND OF THE INVENTION

The present invention relates to a biosensor facilitating rapid and highly accurate quantification of a measuring subject (a subject to be measured) contained in a sample in a simplified manner.

A biosensor has conventionally been proposed in the Japanese Laid-Open Patent Publication Hei 2-062952 as a system for simplified quantification of a specific component in a sample without diluting or stirring a sample solution.

This biosensor is produced by first forming an electrode system comprising a measuring electrode, a counter electrode and a reference electrode on an electrically insulating base plate by using a screen printing method or the like, and then forming an enzyme reaction layer comprising a hydrophilic polymer, an oxidoreductase and an electron mediator. If occasion demands, a buffer is added to this enzyme reaction layer.

When a sample solution containing a substrate is dropped on the enzyme reaction layer of the biosensor thus formed, dissolution of the enzyme reaction layer takes place, which in turn triggers a reaction between the enzyme and the substrate, causing reduction of the electron mediator. Upon completion of the enzyme reaction, the reduced electron mediator is oxidized electrochemically. The concentration of the substrate in the sample solution can be determined from the oxidation current value measured in this oxidizing step.

This biosensor can be used theoretically for measurements of various materials if an appropriate enzyme for each of the materials as the substrate is selected. For example, the use of glucose oxidase as the oxidoreductase can realize a biosensor for measurement of blood glucose level. This sensor is widely applied practically as a glucose sensor. The use of cholesterol oxidase as the oxidoreductase can realize a biosensor for measurement of serum cholesterol.

Serum cholesterol level which serves as the diagnostic standard is the sum of serum cholesterol and cholesterol ester concentrations. Since cholesterol ester cannot serve as a substrate for oxidation by cholesterol oxidase, an additional step of converting cholesterol ester into cholesterol becomes necessary in order to determine serum cholesterol concentrations as the diagnostic standard. Cholesterol esterase is known as an enzyme for catalyzing this process.

Inclusion of this cholesterol esterase together with cholesterol oxidase in the enzyme reaction layer can realize a biosensor for measurement of the total cholesterol concentration in serum.

In the biosensor having such constitution, the enzyme reaction layer is formed by dropping an aqueous reagent solution containing at least an oxidoreductase onto the electrode system and drying the dropped solution. Such biosensor has a problem, when the amount of reagents is large, that the reaction layer is not dissolved quickly after dropping of the sample solution thereonto so that the measurement takes a long time.

Particularly in the cholesterol sensor, two kinds of enzymes, cholesterol oxidase and cholesterol esterase, must be contained in the enzyme reaction layer, as described previously. Therefore, the enzyme reaction layer contains a considerably large amount of reagents, so that dissolution of this layer takes a significantly long time after dropping of the sample solution, which makes it impossible to make rapid measurement.

In order to solve the above-mentioned problem, a biosensor has been proposed in Japanese Laid-Open Patent Publication 2000-039416. The biosensor comprises an insulating base plate, an electrode system including at least a measuring electrode and a counter electrode formed on the base plate, a cover member which is integrated into the base plate and forms a sample solution supply pathway for supplying a sample solution to the electrode system between the cover member and the base plate, and a carrier comprising a fiber for supporting reagents containing at least an oxidoreductase, wherein the carrier is disposed in the sample solution supply pathway.

Also, this biosensor according to another embodiment comprises an insulating base plate, an electrode system including at least a measuring electrode and a counter electrode formed on the base plate, and a carrier comprising a fiber for supporting reagents containing at least an oxidoreductase, wherein the carrier is fixed with an adhesive in the vicinity of the electrode system.

In this biosensor, however, the height of the sample solution supply pathway is required to be at least equal to or greater than the thickness of the carrier, since the carrier is disposed in the sample solution supply pathway. Moreover, the biosensor actually has a structure that the carrier and the electrode system are disposed to face each other, thereby requiring a certain space between the electrode system and the surface of the carrier in order to prevent the contact between them. Thus, the height of the sample solution supply pathway is required to be further greater.

For these reasons, when the carrier is disposed in the sample solution supply pathway, the biosensor requires a sample solution in a relatively large amount in order to fill the sample solution supply pathway with the sample solution. The amount is determined by multiplying the carrier volume calculated from the external dimensions thereof by the porosity of the carrier to obtain a product and by adding to the product the above-mentioned space between the electrode system and the surface of the carrier.

Meanwhile, it is more preferable that the porosity of the carrier is higher in order to improve dissolution of the reagents.

From such characteristics as described, the above-described biosensor tends to need a larger amount of the sample solution for the measurement than the biosensor without a carrier.

Also, especially when the sample solution is blood and the biosensor is provided with a function of filtering blood corpuscle components with a porous material such as a filter paper, the porous material for filtering the blood corpuscle components has sometimes made it difficult for the filtered sample solution to invade into the sample solution supply pathway, since the carrier is disposed in the sample solution supply pathway.

BRIEF SUMMARY OF THE INVENTION

In view of the above problems, an object of the present invention is to provide a biosensor in which dissolution of reagents is improved to enable prompt quantification and reduction of the amount of a sample solution. Further, another object of the present invention is to provide a biosensor in which the sample solution can be introduced readily.

A biosensor in accordance with the present invention comprises an electrically insulating base plate; an electrode system including at least a measuring electrode and a counter electrode formed on the base plate; a cover member, which is integrated into the base plate and forms a sample solution supply pathway for supplying a sample solution to the electrode system between the cover member and the base plate; a reaction reagent system including at least an electron mediator and an oxidoreductase; and a carrier supporting at least the electron mediator or the oxidoreductase of the reaction reagent system, wherein the carrier is partially or wholly disposed outside the sample solution supply pathway.

In the biosensor in accordance with the present invention, it is effective that the carrier has a region supporting at least the electron mediator or the oxidoreductase disposed closer to the electrode system than a region supporting none of the reaction reagent system.

Also, it is effective that the oxidoreductase is cholesterol oxidase.

Further, it is preferable that the reaction reagent system contains an enzyme capable of hydrolyzing cholesterol ester.

It is effective that the enzyme capable of hydrolyzing cholesterol ester is cholesterol esterase.

Furthermore, it is preferable that the reaction reagent system contains a surfactant.

It is effective that the carrier is porous and, further, that the carrier is fibrous or comprises a fiber.

While the novel feature of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

In the biosensor according to the present invention, a reagent including at least one of an electron mediator and an oxidoreductase is supported on a carrier comprising a porous material.

The reagent is supported on the carrier in such a manner that it is adhered to the surface of the porous material constituting the carrier. Thus, the surface area of the reagent in contact with a sample solution becomes larger, resulting in improvement of the dissolution of the reagent into the sample solution.

As the carrier, various ones may be used if it has a function of supporting the reagent and is inactive to the enzyme reaction and electrochemical reaction occurring in the biosensor. For example, a sheet made by laminating a cellulose fiber, a glass fiber or a polymeric compound fiber into a fleece or felt form is preferable.

With regard to the layout of the carrier in the biosensor, various changes are possible.

In one embodiment, the whole carrier is disposed outside the sample solution supply pathway of the cover member while an end of the carrier is brought in contact with the tip end of the sample solution supply pathway.

In another embodiment, a part of the carrier is inserted in the sample solution supply pathway of the cover member.

As in these embodiments, by exposing at least a part of the carrier to outside of the sample solution supply pathway, permeation of the sample solution into the carrier is facilitated, thereby enabling prompt dissolution of the reagent supported on the carrier.

Also, in the case of using a sample solution such as blood containing a solid component which may adversely influence the electrode reaction or the enzyme reaction, at least a part of the carrier may be provided with a region where the reagent is not supported, through which region the sample solution is introduced for permeation in order to filter the solid component.

When the carrier is brought in contact with the sample solution supply pathway of the cover member, it is desirable that the carrier is adhered and secured to either a part of the cover member or a part of the insulating base plate having the electrode system formed thereon, or both thereof.

As the adhesive, it is preferable to use one having such a high viscosity as to prevent permeation into the carrier under the environment of sensor production, one having a poor dissolution into water after adhesion, or one having an electrochemical inactivity in an aqueous solution even if it is soluble in water. For example, it is preferable to use a woodworking adhesive such as the adhesive commercially available under the trade name of Cemedine C from Cemedine Co., Ltd.

As the oxidoreductase to be supported on the carrier, various compounds can be used. For example, glucose oxidase, lactate oxidase, cholesterol oxidase and the like are listed.

When serum cholesterol level is measured, cholesterol oxidase and an enzyme capable of hydrolyzing cholesterol ester are used. As the enzyme capable of hydrolyzing cholesterol ester, cholesterol esterase, lipoprotein lipase and the like are listed. Particularly, cholesterol esterase is advantageous since it can convert cholesterol ester into cholesterol quickly by using a suitable surfactant.

When the enzyme capable of hydrolyzing cholesterol ester is used, it is preferable that a surfactant having the effect of improving the activity of this enzyme is contained in the reagent, which is supported on the whole carrier or a part of the carrier, since the duration of time required for the enzyme reaction can be reduced.

For example, as the surfactant for improving the activity of cholesterol esterase, it is possible to use an arbitrary choice of n-octyl-β-D-thioglucoside, polyethylene glycol monododecyl ether, sodium cholate, dodecyl-β-maltoside, sucrose monolaurate, sodium deoxycholate, sodium taurodeoxycholate, N,N-bis(3-D-gluconeamidopropyl) choleamide, N,N-bis(3-D-gluconeamidopropyl) deoxycholeamide, polyoxyethylene-p-t-octyl phenyl ether (for example, TritonX-100 produced by SIGMA Co., Ltd) and the like.

If the electrode system of the biosensor is formed by using an electrochemically stable metal such as platinum, the obtained oxidation current value is free from an error. However, since such metal is expensive, the electrode system of a disposable sensor is prepared by forming a silver electrode with a silver paste and the like and subsequently coating it with a carbon paste.

However, when the surfactant is contained in the sample solution, the sample solution permeates between carbon particles by the action of the surfactant. As a result, the activity of the carbon electrode may decrease, and the sample solution comes in contact with the silver electrode. Thus, when a voltage is applied on a measuring electrode under such condition, the silver electrode causes an oxidation reaction to generate a current, so that a positive error may be included in the measured current value.

For suppressing such a phenomenon, there is a method that the surface of the electrode system is coated with a hydrophilic polymer. This hydrophilic polymer forms a viscose layer even upon introduction of the sample solution, suppressing the contact of the sample solution with the electrode.

Examples of such hydrophilic polymer include carboxymethylcellulose, polyvinylpyrrolidone, polyvinyl alcohol, ethylcellulose, hydroxypropylcellulose, gelatin, polyacrylic acid and salts thereof, starch and derivatives thereof, maleic anhydride and salts thereof, polyacrylamide, methacrylate resin, poly 2-hydroxyethyl methacrylate and the like.

An enzyme such as an oxidoreductase or cholesterol esterase may be carried so as to cover the above-described hydrophilic polymer layer. In this case, an electron mediator is carried on the above-mentioned carrier.

It is preferable to further form an amphipathic substance layer so as to cover the above-mentioned layer over the electrode system, i.e., the hydrophilic polymer layer or the enzyme layer covering the hydrophilic polymer layer. The amphipathic substance layer is formed by dropping a solution prepared by dissolving an amphipathic substance such as lecithin in an organic solvent and subsequently drying it.

Although such amphipathic substance layer is not necessary for the enzyme reaction and the electrode reaction, formation of this layer allows for smooth introduction of the sample solution. Preferable examples of such amphipathic substance include phospholipid such as lecithin.

Further, a surfactant layer may be provided on the portion of the cover member facing the sample solution supply pathway or the surface of the electrode system. This layer allows the sample solution, which has completed to react or is reacting with the reaction reagent system contained in the carrier, to smoothly permeate the sample solution supply pathway, thereby to reach the electrode system.

The surfactant used for such purpose is desirably selected from the above-listed surfactants for improving the activity of cholesterol esterase, but any surfactant other than these may be used if it does not disturb the reaction system.

When the surfactant layer is provided, it is essential to form the above-mentioned hydrophilic polymer layer covering the surface of the electrode system. In this case, the surfactant layer must be formed by dissolving a surfactant in a solvent which does not dissolve the hydrophilic polymer layer to obtain a solution, dropping the solution prepared so as to cover the hydrophilic polymer layer, and subsequently drying it.

As the electron mediator to be supported on the carrier, any water-soluble compound which can mediate electron transfer between the enzyme and the electrode such as potassium ferricyanide, p-benzoquinone, phenazine methosulfate or ferrocene derivative (oxidized form) may be used.

As the measuring method of the oxidation current, a two-electrode system composed only of a measuring electrode and a counter electrode or a three-electrode system further comprising a reference electrode is applicable, and the three-electrode system can give more accurate measurement results.

Figure 1:
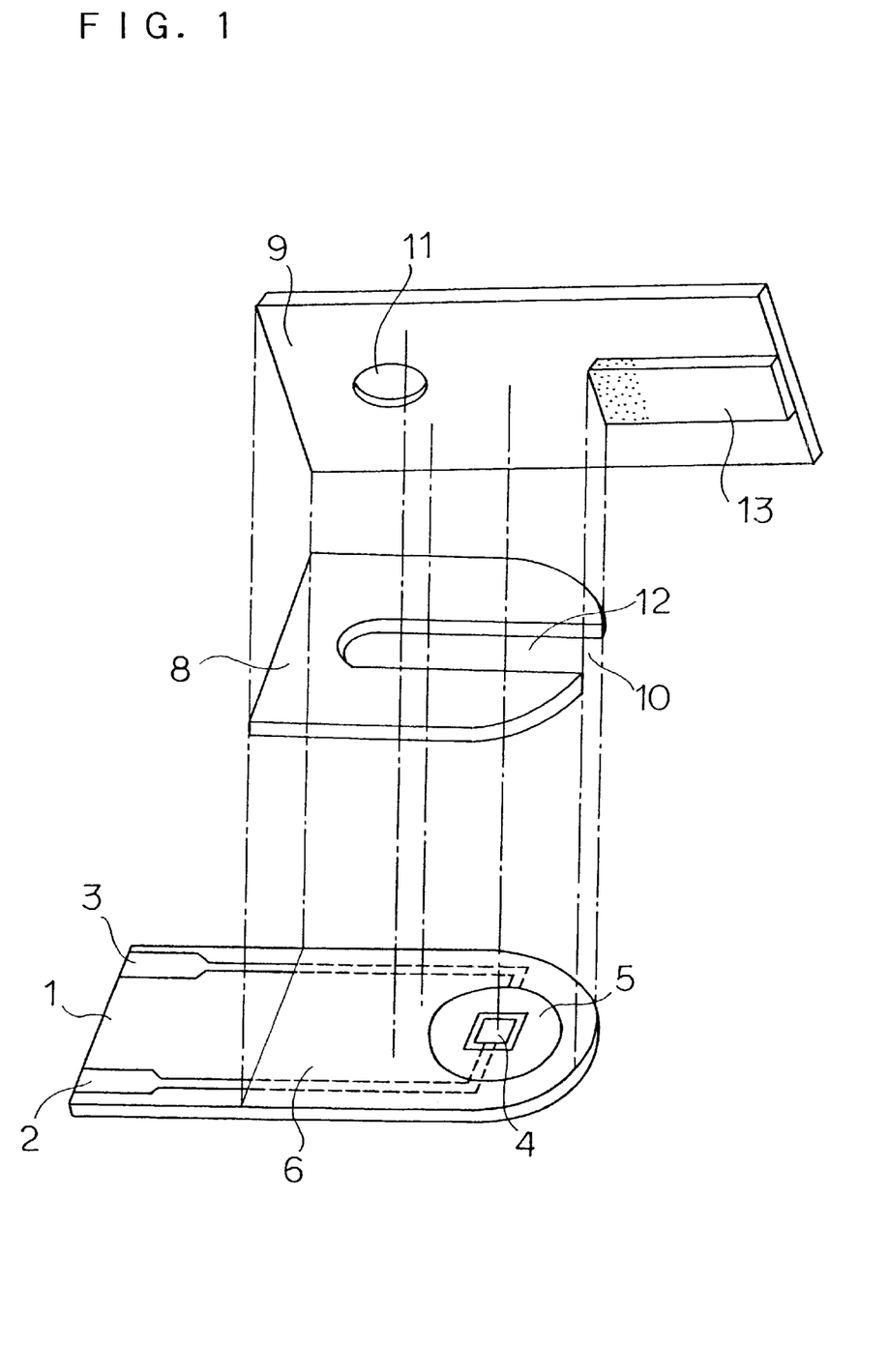
FIG. 1 is an exploded perspective view of a biosensor in accordance with one example of the present invention.

In the following, the present invention will be described more specifically, referring to concrete examples, although the present invention is not limited to these examples. FIG. 1 is an exploded perspective view of the biosensor according to one example of the present invention.

As shown in FIG. 1, numeral 1 represents an electrically insulating base plate made of polyethylene terephthalate, and leads 2 and 3 and the ground for an electrode system are formed on this base plate 1 by printing a silver paste using a screen printing method. On the base plate 1, an electrically conductive carbon paste containing a resin binder is further printed to form the electrode system containing a measuring electrode 4 and a counter electrode 5, and an electrically insulating paste is printed to form an electrically insulating layer 6. The measuring electrode 4 is connected to the lead 2, and the counter electrode 5 is connected to the lead 5, respectively. The electrically insulating layer 6 allows the areas of exposed portions of the measuring electrode 4 and the counter electrode 5 to be constant and covers the leads partially.

The electrically insulating base plate 1 with the electrode system formed thereon, a cover 9 having an air vent 11, a spacer 8 and a carrier 13 supporting a reagent are adhered under the positional relation as shown by the dotted chain lines in FIG. 1 to form a biosensor.

In the biosensor having such constitution, a space constituting a sample solution supply pathway is formed in a slit 12 of the spacer 8 between the base plate 1 and the cover 9.

A sample solution is introduced into the sensor from an opening 10 forming a port of the sample solution supply pathway. In this example, the length from the opening to the edge of the air vent 11, which is closer to the opening, is 4.5 mm, the width of the slit 2.0 mm, and the depth of the slit 0.1 to 0.3 mm.

These dimensions are provided in order to define the dimensions of carriers which will be described below, but the dimensions of the carriers are not limited to those given above.

Figure 2:
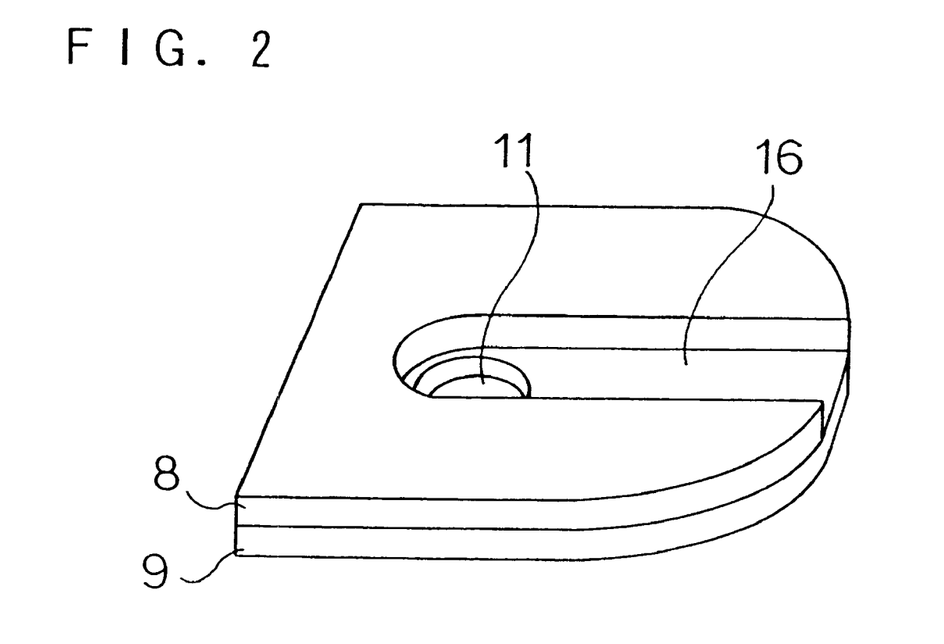
FIG. 2 is a perspective view of a cover member formed by integrating a cover and a spacer of the biosensor shown in FIG. 1, being arranged upside down against the view of FIG. 1.

FIG. 2 is a perspective view of a cover member formed by laying the spacer 8 on top of the cover 9, which is arranged upside down against the view of FIG. 1. By combining this cover member with the base plate, the space constituting the sample solution supply pathway is formed.

Figure 3:
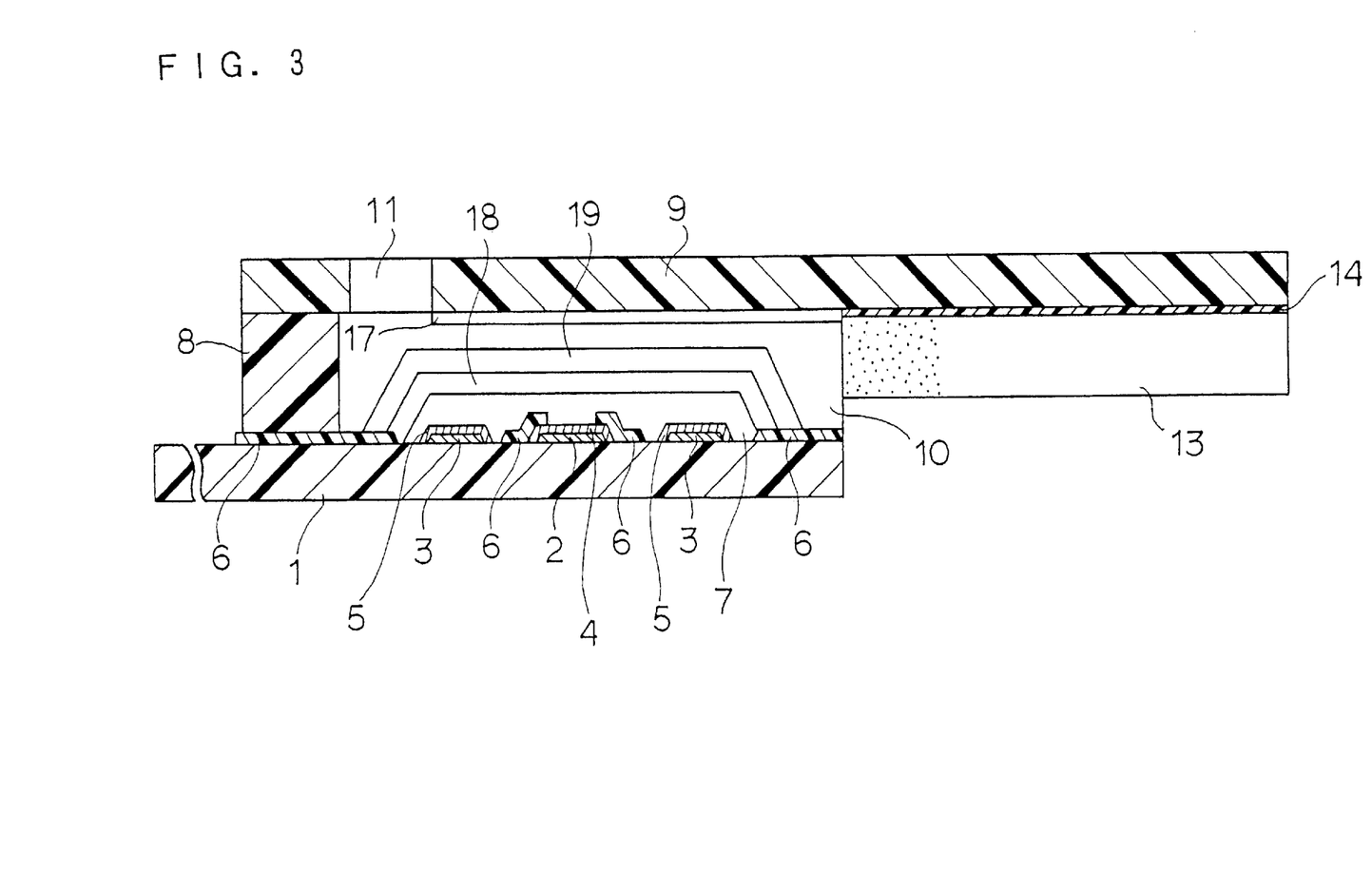
FIG. 3 is a longitudinal sectional view of the main parts of the biosensor shown in FIG. 1.

FIG. 3 is a longitudinal sectional view of the biosensor according to one example of the present invention. In the same manner as in FIG. 1, the electrically insulating base plate 1 is provided with the electrode system, over which a hydrophilic polymer layer 7 is formed, an enzyme layer 18 comprising cholesterol oxidase and cholesterol esterase is further formed so as to coat this hydrophilic polymer layer 7, and a surfactant layer 19 comprising Triton X-100 is further formed thereon.

Furthermore, a lecithin layer 17 is disposed on the inner surface of the cover 9 constituting the sample solution supply pathway, and the carrier 13 supporting a reagent is adhered to the cover 9 with an adhesive 14 so as to come in contact with the sample solution supply port 10.

Figure 4:
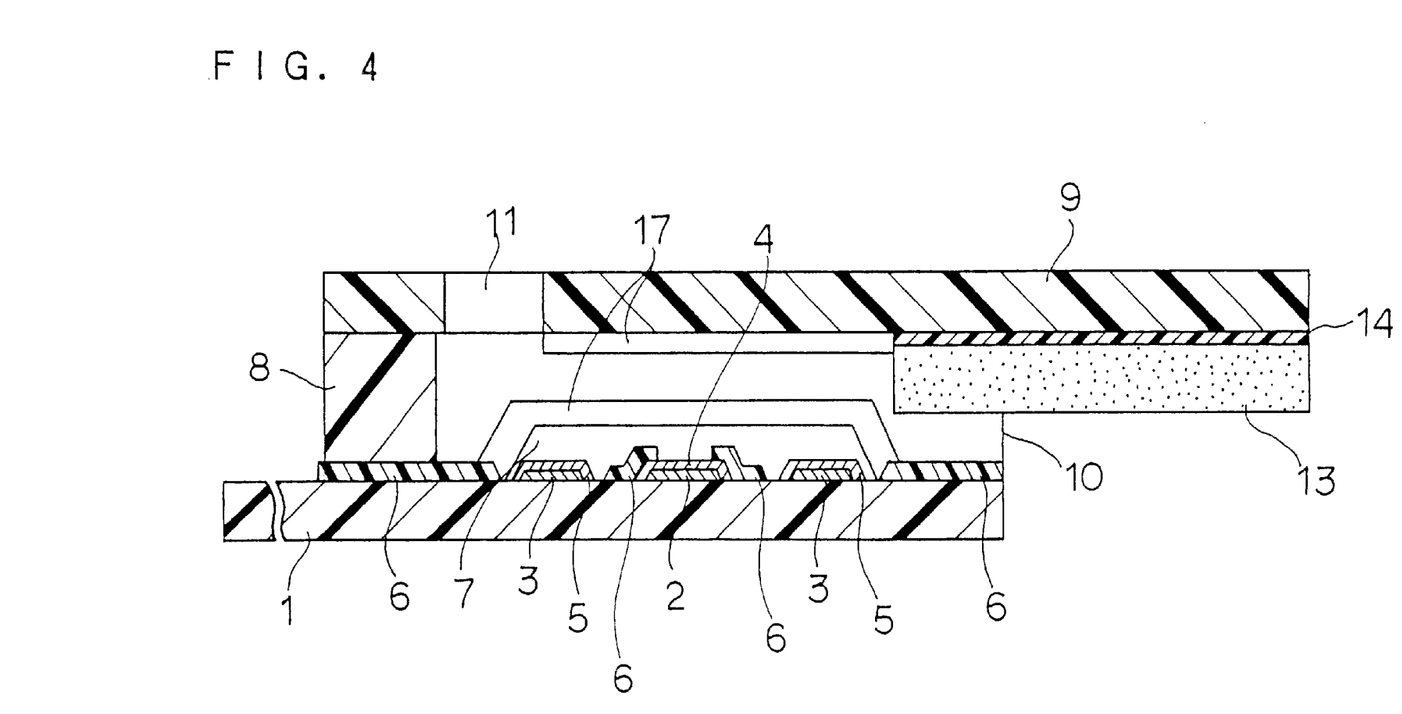
FIG. 4 is a longitudinal sectional view of the main parts of a biosensor in accordance with another example of the present invention.

FIG. 4 is a longitudinal sectional view of the biosensor according to another example of the present invention. In the same manner as in FIG. 3, the electrically insulating base plate 1 is provided with the electrode system, over which a hydrophilic polymer layer 7 and a lecithin layer 17 are formed. Further, the carrier 13 supporting reagent is fixed with an adhesive 14 to the cover 9 from the vicinity of the sample solution supply port 10 to outside of the sample solution supply pathway in such a manner that a part of the carrier is inserted into the sample solution supply pathway.

Figure 5:
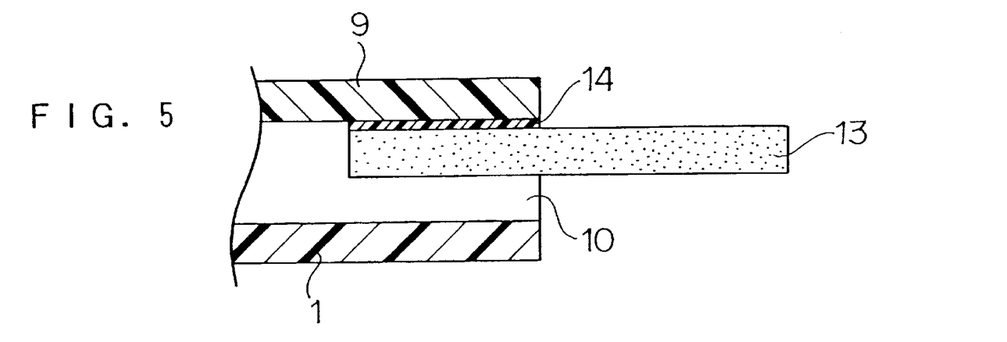
FIG. 5 is a longitudinal sectional view of the main parts of a biosensor in accordance with still another example of the present invention.
Figure 6:
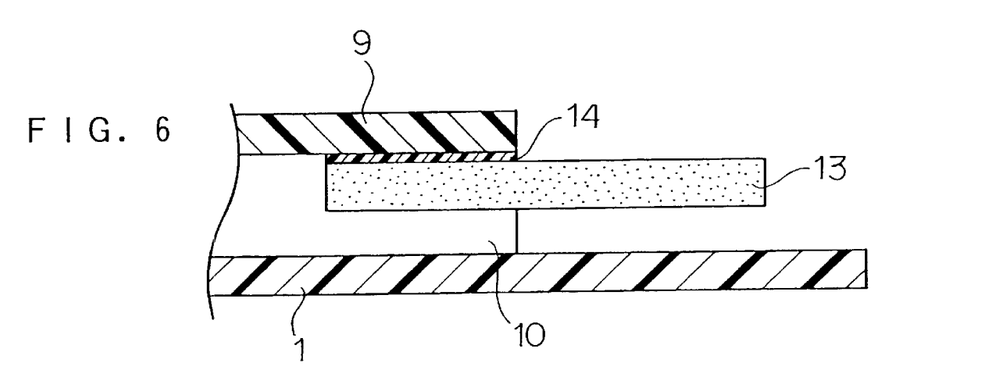
FIG. 6 is a longitudinal sectional view of the main parts of a biosensor in accordance with another example of the present invention.
Figure 7:
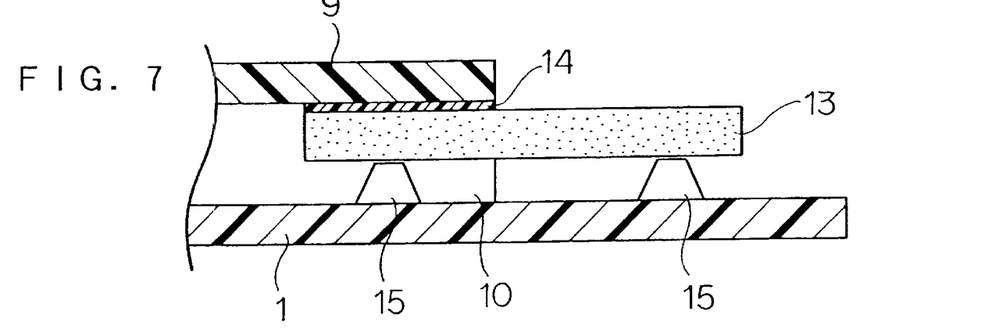
FIG. 7 is a longitudinal sectional view of the main parts of a biosensor in accordance with still another example of the present invention.

FIGS. 5 to 7 are a longitudinal sectional view of a part of the biosensor according to another example of the present invention, with the omission of the electrode system, the hydrophilic polymer layer and the surfactant layer.

In the biosensor illustrated in FIG. 5, a part of the carrier 13 is fixed with an adhesive 14 to the inner surface of the cover constituting the sample solution supply pathway. The end of the carrier 13 exposed to outside extends beyond the end of the insulating base plate at the sample solution supply port side. This structure allows the carrier to be supplied with a sample from the upper side (i.e., the cover side) or the lower side (i.e., the insulating base plate side).

In the biosensor illustrated in FIG. 6, the end of the insulating base plate at the sample solution supply port side extends beyond the end of the carrier 13 exposed to outside, as opposed to the layout in FIG. 1. This structure allows the sample to be introduced and carried on the insulating base plate, which is advantageous when permeation of the sample such as blood into the carrier takes a relatively long time.

In the biosensor illustrated in FIG. 7, the carrier 13 is secured by at least one or more protrusion(s) 15 formed on the insulating base plate 1 constituting the sample solution supply pathway. This structure enables the carrier 13 to be secured without the use of an adhesive. Also, formation of at least one protrusion 15 in a sleeper-like shape makes it possible to prevent the phenomenon that the sample solution directly reaches the electrode system through only the periphery of the carrier so that it does not dissolve the reagent supported on the carrier sufficiently.

Example 1

In this example, a biosensor having the constitution in FIG. 3 was manufactured as described below.

First, on the electrode system on the base plate 1 in FIG. 1, a 0.5 wt % aqueous solution of sodium salt of carboxymethylcellose (hereinafter referred to as "CMC") which is a hydrophilic polymer was dropped and dried in a hot air drier for 10 minutes at 50° C. to form a CMC layer 7.

Subsequently, 2 µl of a mixed solution obtained by mixing 400 unit/ml cholesterol oxidase (hereinafter referred to as "ChOx") and 2 kilo unit cholesterol esterase (hereinafter referred to as "ChE") was dropped to cover the CMC layer 7 to form an enzyme layer 18.

Further, 1 µl of a 5.0% ethanol solution of Triton X-100 was dropped to cover the enzyme layer 18, and dried to form a surfactant layer 19. The surfactant layer 19 was provided to facilitate the smooth dispersion of the sample solution throughout the electrode system, and TritonX-100 was used to improve the activity of ChE. Furthermore, a lecithin layer 17 was provided on the inner surface of the cover constituting a sample solution supply pathway.

Also, a felt-form glass filter of 0.2 mm in thickness, 2 mm in width and 10 mm in length was prepared. The glass filter was cooled by liquid nitrogen, and an aqueous solution containing potassium ferricyanide as an electron mediator was then dropped on one tip end of the glass filter. This solution froze immediately after the dropping thereof and therefore did not disperse throughout the glass filter, since the glass filter had been cooled by the liquid nitrogen.

Accordingly, the potassium ferricyanide solution was dropped and allowed to permeate about 2 mm from the tip end of the glass filter. Thereafter, the glass filter was dried under reduced pressure for about 4 hours in a freeze dryer. As a result, 0.33 µmol of potassium ferricyanide was carried per 1 mm$^2$ in the area of 2 mm from the tip end of the glass filter.

As illustrated in FIG. 1, the glass filter supporting potassium ferricyanide in a portion thereof in the above-described manner was adhered and fixed to the cover 9 as a carrier. In this process, the carrier was disposed in such a manner that the end portion supporting potassium ferricyanide was brought in contact with the tip end of the sample solution supply pathway. Then, this cover member and the base plate 1 were adhered under the positional relation as shown by the dotted chain lines in FIG. 1 to form a biosensor.

Herein, the depth of a slit 12 of the sample solution supply pathway was made 0.1 mm.

10 µl of a sample solution was supplied to the biosensor thus formed from the other end of the carrier 13 not supporting potassium ferricyanide such that it was absorbed therefrom. As the sample solution, blood or a mixed solution prepared by adding blood corpuscle to a standard serum solution, which is diluted while maintaining the osmotic pressure at a constant level, was used.

As a result, before the blood corpuscle component of the sample solution reached the portion of the carrier supporting potassium ferricyanide, the filtered liquid component of the sample solution dissolved potassium ferricyanide supported on the carrier and invaded into the sample solution supply pathway from the sample solution supply port, so that the surface of the electrode system was filled with the sample solution. Three minutes after the supply of the sample solution, a pulse voltage of +0.5 V was applied to the measuring electrode in the anodic direction, using the counter electrode as a reference. Five seconds after this voltage application, the current value flowing between the measuring electrode and the counter electrode was measured.

As a result, the measured value showed a current response depending on the total cholesterol concentration in the sample solution.

Example 2

In this example, a biosensor having the constitution shown in FIG. 4 was manufactured as described below.

In the same manner as in Example 1, a CMC layer 7 and a lecithin layer 17 were formed over the electrode system on the base plate 1 in FIG. 1. The lecithin layer 17 was formed also on an inner surface of the cover constituting the sample solution supply pathway.

Next, potassium ferricyanide, ChOx, ChE and TritonX-100 were allowed to be supported on a felt-form glass filter of 0.2 mm in thickness, 2 mm in width and 4.5 mm in length. Herein, TritonX-100, which is a surfactant, was used in order to improve the activity of ChE. The supported amount of potassium ferricyanide was 0.33 µmol per 1 mm$^2$ of the glass filter. The supported amount of ChOx was 0.1 unit per 1 mm$^2$ of the glass filter. Also, the supported amounts of ChE and TritonX-100 were 1 unit and 0.15 mg, respectively.

A woodworking adhesive (the adhesive commercially available under the trade name of Cemedine C from Cemedine Co., Ltd.) as an adhesive 14 was applied to the inner surface of the cover, to which the glass filer was then adhered and fixed as a carrier such that one tip end of the carrier was disposed at a position, which was 1 mm inner from the sample solution supply port. As a result, a biosensor was produced so as to have a constitution that most of the carrier was exposed to outside of the sample solution supply pathway.

A standard serum or a solution prepared by diluting a standard serum with physiological saline was supplied as a sample solution to the biosensor thus produced by introducing it to a portion of the carrier which was exposed to outside of the sample solution supply pathway. Then, the response value was measured in the same manner as in Example 1. As a result, the measured value showed a favorable current response depending on the total cholesterol concentration. In this example, the dissolution of the reagents in the carrier was excellent. Moreover, the invasion of the sample solution into the sample solution supply pathway was also very smooth.

As described above, the present invention allows the sample solution to be introduced smoothly even when the amount of the sample solution is small and improves the dissolution of the reagents. Therefore, it is possible to make prompt quantification according to the present invention.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A biosensor comprising: an insulating base plate; an electrode system including at least a measuring electrode and a counter electrode formed on said base plate; a cover member integrated into said base plate to form a sample solution supply pathway for supplying a sample solution to said electrode system between said cover member and said base plate; a reaction reagent system including at least an electron mediator and an oxidoreductase; and a carrier supporting at least the electron mediator or the oxidoreductase of said reaction reagent system, wherein said carrier is partially or wholly disposed outside said sample solution supply pathway.

2. The biosensor in accordance with claim 1, wherein said carrier has a region supporting at least the electron mediator or the oxidoreductase disposed closer to said electrode system than a region supporting none of said reaction reagent system.

3. The biosensor in accordance with claim 1, wherein said oxidoreductase is cholesterol oxidase.

4. The biosensor in accordance with claim 1, wherein said reaction reagent system contains an enzyme capable of hydrolyzing cholesterol ester.

5. The biosensor in accordance with claim 4, wherein said enzyme capable of hydrolyzing cholesterol ester is cholesterol esterase.

6. The biosensor in accordance with claim 4, wherein said reaction reagent system contains a surfactant.

7. The biosensor in accordance with claim 1, wherein said carrier is porous.

8. The biosensor in accordance with claim 7, wherein said carrier is fibrous.

9. The biosensor of claim 1, wherein an end portion of said cover member extends beyond a end portion of said base plate.

10. The biosensor of claim 1, wherein an end portion of said base plate extends beyond an end portion of said cover member.

11. A biosensor comprising:

an insulating base plate;

an electrode system including at least a measuring electrode and a counter electrode formed on said base plate;

a spacer member disposed on said base plate, said spacer member having a slit-like opening;

a cover member disposed on said spacer member, said slit-like opening of said spacer member defining a sample solution supply pathway for supplying a sample solution to said electrode system;

a reaction reagent system including at least an electron mediator and an oxidoreductase; and a carrier supporting at least the electron mediator or the oxidoreductase of said reaction reagent system, wherein said carrier is partially or wholly disposed outside said sample solution supply pathway.

12. The biosensor of claim 11, wherein an end portion of said cover member extends beyond a end portion of said base plate.

13. The biosensor of claim 11, wherein an end portion of said base plate extends beyond an end portion of said cover member.

* * * * *